US010048591B2

(12) United States Patent
Smirnov et al.

(10) Patent No.: US 10,048,591 B2
(45) Date of Patent: *Aug. 14, 2018

(54) CATADIOPTRIC ILLUMINATION SYSTEM FOR METROLOGY

(71) Applicant: ASML HOLDING N.V., Veldhoven (NL)

(72) Inventors: Stanislav Y. Smirnov, Danbury, CT (US); Yevgeniy Konstantinovich Shmarev, Lagrangeville, NY (US)

(73) Assignee: ASML HOLDING N.V., Veldhoven (NL)

( * ) Notice: Subject to any disclaimer, the term of this patent is extended or adjusted under 35 U.S.C. 154(b) by 708 days.

This patent is subject to a terminal disclaimer.

(21) Appl. No.: 14/592,755

(22) Filed: Jan. 8, 2015

(65) Prior Publication Data
US 2015/0116719 A1 Apr. 30, 2015

Related U.S. Application Data

(63) Continuation of application No. 13/164,196, filed on Jun. 20, 2011, now Pat. No. 9,069,260.
(Continued)

(51) Int. Cl.
G01N 22/00 (2006.01)
G03F 7/20 (2006.01)
(Continued)

(52) U.S. Cl.
CPC ..... *G03F 7/70225* (2013.01); *G01N 21/4738* (2013.01); *G01N 21/4788* (2013.01);
(Continued)

(58) Field of Classification Search
CPC ............ G03F 7/70225; G01N 21/4738; G02B 17/08; G02B 17/0876
(Continued)

(56) References Cited

U.S. PATENT DOCUMENTS 3,326,621 A 6/1967 Berggren De Nygorden
4,214,815 A 7/1980 Shimokura
(Continued)

FOREIGN PATENT DOCUMENTS

CN 101349804 1/2009
EP 2 017 662 1/2009
(Continued)

OTHER PUBLICATIONS

Singapore Examination Report dated Jun. 14, 2016 in corresponding Singapore Patent Application No. 201102637-4.
(Continued)

*Primary Examiner* — Tri Ton
*Assistant Examiner* — Rebecca C Bryant
(74) *Attorney, Agent, or Firm* — Pillsbury Winthrop Shaw Pittman LLP

(57) ABSTRACT

A catadioptric optical system operates in a wide spectral range. In an embodiment, the catadioptric optical system includes a first reflective surface positioned and configured to reflect radiation; a second reflective surface positioned and configured to reflect radiation reflected from the first reflective surface as a collimated beam, the second reflective surface having an aperture to allow transmission of radiation through the second reflective surface; and a channel structure extending from the aperture toward the first reflective surface and having an outlet, between the first reflective surface and the second reflective surface, to supply radiation to the first reflective surface.

20 Claims, 10 Drawing Sheets

Related U.S. Application Data

(60) Provisional application No. 61/357,411, filed on Jun. 22, 2010.

(51) Int. Cl.
*G01N 21/47* (2006.01)
*G01N 21/95* (2006.01)
*G01N 21/956* (2006.01)
*G02B 21/00* (2006.01)
*G02B 21/04* (2006.01)
*G02B 17/08* (2006.01)

(52) U.S. Cl.
CPC ....... *G01N 21/9501* (2013.01); *G01N 21/956* (2013.01); *G02B 17/08* (2013.01); *G02B 21/0016* (2013.01); *G02B 21/04* (2013.01); *G03F 7/70625* (2013.01); *G01N 2201/062* (2013.01); *G01N 2201/0636* (2013.01); *G01N 2201/0638* (2013.01); *G02B 17/0876* (2013.01)

(58) Field of Classification Search
USPC .......... 356/237.3–237.5, 446; 359/365, 649, 359/731
See application file for complete search history.

(56) References Cited

U.S. PATENT DOCUMENTS

| | | | |
|---|---|---|---|
| 4,749,840 A | 6/1988 | Piwczyk | |
| 5,559,338 A | 9/1996 | Elliott et al. | |
| 5,668,669 A | 9/1997 | Ohtake et al. | |
| 6,285,476 B1 | 9/2001 | Carlson et al. | |
| 7,280,283 B1 | 10/2007 | Kasai | |
| 7,505,211 B2 | 3/2009 | Horneber | |
| 7,630,136 B2 | 12/2009 | Ryzhikov et al. | |
| 7,633,689 B2 | 12/2009 | Shmarev et al. | |
| 2004/0095573 A1 | 5/2004 | Tsai et al. | |
| 2006/0018012 A1 | 1/2006 | Smith et al. | |
| 2006/0109559 A1 | 5/2006 | Hudyma et al. | |
| 2007/0053058 A1 | 3/2007 | Angelini et al. | |
| 2007/0115564 A1 | 5/2007 | Maresse | |
| 2009/0073392 A1 | 3/2009 | Mann et al. | |
| 2009/0244701 A1 | 10/2009 | Gohman | |

FOREIGN PATENT DOCUMENTS

| | | |
|---|---|---|
| JP | S62-210415 | 9/1987 |
| JP | H10-267846 | 10/1998 |
| JP | 2009-044143 | 2/2009 |
| KR | 10-2009-0009159 | 1/2009 |
| TW | 200912384 | 3/2009 |
| WO | 87/06718 | 11/1987 |
| WO | 2006/104748 | 10/2006 |
| WO | 2006/105122 | 10/2006 |

OTHER PUBLICATIONS

Taiwan Office Action dated Oct. 7, 2015 in corresponding Taiwan Patent Application No. 100114963.
Japanese Office Action dated Jan. 28, 2015 in corresponding Japanese Patent Application No. 2011-133105.
European Search Report dated Jul. 28, 2011 in European Patent Application No. EP 11 16 1458.
Chinese Office Action dated Aug. 26, 2014 in corresponding Chinese Patent Application No, 201110169124.9.
Korean Office Action dated Jul. 20, 2017 in corresponding Korean Patent Application No. 10-2011-0060105.

CATADIOPTRIC ILLUMINATION SYSTEM FOR METROLOGY

This application is a continuation of U.S. patent application Ser. No. 13/164,196, filed on Jun. 20, 2011, which application claims priority and benefit under 35 U.S.C. § 119(e) to U.S. Provisional Patent Application No. 61/357,411, filed on Jun. 22, 2010. The content of each of the foregoing applications is incorporated herein in its entirety by reference.

FIELD

The present invention is generally directed to optical systems, and more particularly to catadioptric optical systems.

BACKGROUND

A lithographic apparatus is a machine that applies a desired pattern onto a substrate or part of a substrate. A lithographic apparatus can be used, for example, in the manufacture of flat panel displays, integrated circuits (ICs) and other devices involving fine structures. In a conventional apparatus, a patterning device, which can be referred to as a mask or a reticle, can be used to generate a circuit pattern corresponding to an individual layer of an IC, flat panel display, or other device. This pattern can be transferred onto all or part of the substrate (e.g., a glass plate, a wafer, etc.), by imaging onto a layer of radiation-sensitive material (e.g., resist) provided on the substrate.

The patterning device can be used to generate, for example, an IC pattern. The patterning device can additionally or alternatively be used to generate other patterns, for example a color filter pattern or a matrix of dots. Instead of a mask, the patterning device can be a patterning array that comprises an array of individually controllable elements. The pattern can be changed more quickly and for less cost in such a system compared to a mask-based system.

After patterning the substrate, measurements and inspection are typically performed. The measurement and inspection step typically serves two purposes. First, it is desirable to detect any target areas where the pattern in the developed resist is faulty. If a sufficient number of target areas are faulty, the substrate can be stripped of the patterned resist and re-exposed, hopefully correctly, rather than making the fault permanent by carrying out a process step, e.g., an etch, with a faulty pattern. Second, the measurements may allow errors in the lithographic apparatus, e.g., illumination settings or exposure dose, to be detected and corrected for in subsequent exposures.

However, many errors in the lithographic apparatus cannot easily be detected or quantified from the patterns printed in resist. Detection of a fault does not always lead directly to its cause. Thus, a variety of off-line procedures (i.e., procedures carried out in addition to normal processing of the substrate) for detecting and measuring errors in the lithographic apparatus are known. These may involve replacing the substrate with a measuring device or carrying out exposures of special test patterns, e.g., at a variety of different machine settings. Such off-line techniques take time, often a considerable amount, reducing production time and during which the end products of the apparatus will be of an unknown quality until the measurement results are made available. In-line measurement and inspection procedures (i.e., procedures carried out during the normal processing of the substrate) are known.

Optical metrology techniques may be used to perform the measurements and inspection. For example, scatterometry is an optical metrology technique that can be used for measurements of critical dimension (CD) and overlay. There are two main scatterometry techniques:

(1) Spectroscopic scatterometry measures the properties of scattered radiation at a fixed angle as a function of wavelength, usually using a broadband light source, such as a xenon, deuterium, or halogen based light source such as a xenon arc lamp. The fixed angle can be normally incident or obliquely incident.

(2) Angle-resolved scatterometry measures the properties of scattered radiation at a fixed wavelength as a function of angle of incidence, usually using a laser as a single wavelength light source.

Using scatterometry the structure giving rise to a reflected spectrum is reconstructed, e.g., using real-time regression or by comparison to a library of patterns derived by simulation. Reconstruction involves minimization of a cost function. Both approaches calculate the scattering of light by periodic structures. The most common technique is Rigorous Coupled-Wave Analysis (RCWA), though radiation scattering can also be calculated by other techniques, such as Finite Difference Time Domain (FDTD) or Integral Equation techniques.

SUMMARY

Known scatterometers, however, have one or more drawbacks. For example, conventional scatterometers only detect one wavelength at a time. As a result, spectra with more than one wavelength have to be time-multiplexed, which increases the total acquisition time taken to detect and process the spectra.

Accordingly, it is desirable to, for example, to have a metrology tool capable of handling a wide range of wavelengths.

According to an embodiment of the present invention, there is provided a metrology tool, comprising an objective to deliver radiation to a surface and to receive radiation redirected by the surface; a detector to receive the redirected radiation from the objective; and an illumination system to deliver the radiation for redirection to the objective, the illumination system comprising a catadioptric optical system. Use of a catadioptric optical system can facilitate a tool handling a wide range of wavelengths.

According to an embodiment of the present invention, there is provided a catadioptric optical system, comprising: a first reflective surface positioned and configured to reflect radiation; a second reflective surface positioned and configured to reflect radiation reflected from the first reflective surface as a collimated beam, the second reflective surface having an aperture to allow transmission of radiation through the second reflective surface; and a channel structure extending from the aperture toward the first reflective surface and having an outlet, between the first reflective surface and the second reflective surface, to supply radiation to the first reflective surface.

According to an embodiment of the present invention, there is provided a metrology method, comprising: delivering radiation to a surface using an objective; receiving radiation redirected by the surface using the objective; detecting a parameter of the surface using the redirected radiation from the objective; and delivering the radiation for redirection to the objective using a catadioptric optical system.

Further embodiments, features, and advantages of the present invention, as well as the structure and operation of the various embodiments of the present invention, are described in detail below with reference to the accompanying drawings.

BRIEF DESCRIPTION OF THE DRAWINGS

The accompanying drawings, which are incorporated herein and form part of the specification, illustrate the present invention and, together with the description, further serve to explain the principles of the invention and to enable a person skilled in the relevant art(s) to make and use the invention.

Figure 1:
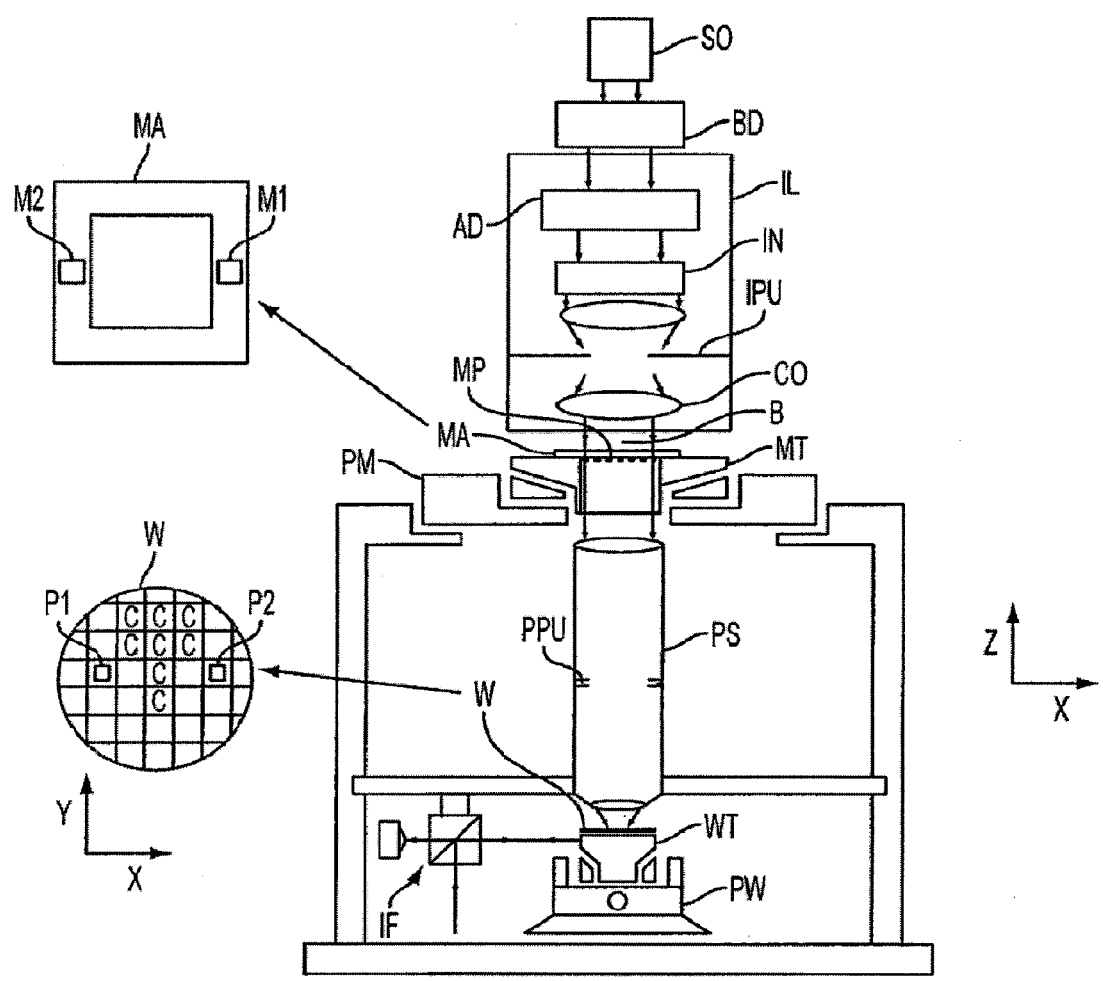
FIG. 1 depicts a lithographic projection apparatus according to an embodiment of the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

In the specification, reference to "one embodiment", "an embodiment", "an example embodiment", etc., indicates that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

DETAILED DESCRIPTION

Before providing additional details of optical systems according to one or more embodiments of the present invention, it is first helpful to describe an example lithography environment and scatterometery system in which such optical systems may be used.

Example Lithography Environment

FIG. 1 depicts a lithographic apparatus according to an embodiment of the present invention. The apparatus of FIG. 1 comprises an illuminator IL, a support structure MT, a substrate table WT, and a projection system. As herein depicted in FIG. 1, the apparatus is of a transmissive type (e.g., employing refractive optical elements in the projection system). Alternatively, the apparatus can be of a reflective type (e.g., employing substantially only reflective elements in the projection system).

The illuminator IL is configured to condition a radiation beam B (e.g., a beam of UV radiation as provided by a mercury arc lamp, or a beam of DUV radiation generated by a KrF excimer laser or an ArF excimer laser). The illuminator IL may include various types of optical components, such as refractive, reflective, diffractive, magnetic, electromagnetic, electrostatic or other types of optical components, or any combination thereof, for directing, shaping, or controlling radiation.

The support structure (e.g., a mask table) MT is constructed to support a patterning device (e.g., a mask) MA having a patterning device pattern MP and connected to a first positioner PM configured to accurately position the patterning device in accordance with certain parameters.

The substrate table (e.g., a wafer table) WT is constructed to hold a substrate (e.g., a resist coated wafer) W and connected to a second positioner PW configured to accurately position the substrate in accordance with certain parameters.

The projection system (e.g., a refractive projection lens system) PS is configured to project the radiation beam B modulated with the pattern MP of the patterning device MA onto a target portion C (e.g., comprising one or more dies) of the substrate W. The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein can be considered as synonymous with the more general term "projection system." The projection system can image the pattern of the patterning device, such that the pattern is coherently formed on the substrate. Alternatively, the projection system can image secondary sources for which the elements of the patterning device act as shutters. In this respect, the projection system can comprise an array of focusing elements such as a micro lens array (known as an MLA) or a Fresnel lens array to form the secondary sources and to image spots onto the substrate. The array of focusing elements (e.g., MLA) comprises at least 10 focus elements, at least 100 focus elements, at least 1,000 focus elements, at least 10,000 focus elements, at least 100,000 focus elements, or at least 1,000,000 focus elements.

The support structure MT holds a patterning device MA. It holds the patterning device MA in a manner that depends on the orientation of the patterning device MA, the design of the lithographic apparatus, and other conditions, such as for example whether or not the patterning device MA is held in a vacuum environment. The support structure MT may be a frame or a table, for example, which may be fixed or movable as required. The support structure MT may ensure that the patterning device MA is at a desired position, for example with respect to the projection system PA. Any use of the terms "reticle" or "mask" herein may be considered synonymous with the more general term "patterning device."

The term "patterning device" used herein should be broadly interpreted as referring to any device that can be used to modulate the cross-section of a radiation beam (e.g., impart a radiation beam 13 with a pattern in its cross-section), such as to create a pattern in a target portion of the substrate. The devices can be either static patterning devices (e.g., masks or reticles) or dynamic (e.g., arrays of programmable elements) patterning devices. Examples of such patterning devices include reticles, programmable mirror arrays, laser diode arrays, light emitting diode arrays, grating light valves, and LCD arrays It should be noted that the pattern imparted to the radiation beam B may not exactly correspond to the desired pattern in the target portion C of the substrate W, for example if the pattern includes phase-shifting features or so called assist features. Similarly, the pattern eventually generated on the substrate may not correspond to the pattern formed at any one instant on an array of individually controllable elements. This can be the case in an arrangement in which the eventual pattern formed on each part of the substrate is built up over a given period of time or a given number of exposures during which the pattern on the array of individually controllable elements and/or the relative position of the substrate changes.

Generally, the pattern created on the target portion of the substrate will correspond to a particular functional layer in a device being created in the target portion, such as an integrated circuit or a flat panel display (e.g., a color filter layer in a flat panel display or a thin film transistor layer in a flat panel display).

Referring to FIG. 1, the illuminator IL receives a radiation beam from a radiation source SO, such as for example a mercury-arc lamp for providing g-line or i-line UV radiation, or an excimer laser for providing DUV radiation of a wavelength of less than about 270 nm, such as for example about 248, 193, 157, and 126 nm. The radiation source provides radiation having a wavelength of at least 5 nm, at least 10 nm, at least 11-13 nm, at least 50 nm, at least 100 nm, at least 150 nm, at least 175 nm, at least 200 nm, at least 250 nm, at least 275 nm, at least 300 nm, at least 325 nm, at least 350 nm, or at least 360 nm. Alternatively, the radiation provided by radiation source SO has a wavelength of at most 450 nm, at most 425 nm, at most 375 nm, at most 360 nm, at most 325 nm, at most 275 nm, at most 250 nm, at most 225 nm, at most 200 nm, or at most 175 nm. The radiation can have a wavelength including 436 nm, 405 nm, 365 nm, 355 nm, 248 nm, 193 nm, 157 nm, and/or 126 nm.

The source SO and the lithographic apparatus may be separate entities, for example when the source SO is an excimer laser. In such cases, the source is not considered to form part of the lithographic apparatus and the radiation beam B is passed from the source SO to the illuminator IL with the aid of a beam delivery system BD comprising, for example, suitable directing mirrors and/or a beam expander. In other cases the source SO may be an integral part of the lithographic apparatus, for example when the source SO is a mercury lamp. The source SO and the illuminator IL, together with the beam delivery system BD if required, may be referred to as a radiation system.

The illuminator IL may comprise an adjuster AD to adjust the angular intensity distribution of the radiation beam at the patterning device level. Generally, at least the outer and/or inner radial extent (commonly referred to as σ-outer and σ-inner, respectively) of the intensity distribution in a pupil plane IPU of the illuminator can be adjusted. In addition, the illuminator IL can comprise various other components, such as an integrator IN and a condenser CO. The illuminator can be used to condition the radiation beam to have a desired uniformity and intensity distribution in its cross-section at the patterning device level. The illuminator IL, or an additional component associated with it, can also be arranged to divide the radiation beam into a plurality of sub-beams that can, for example, each be associated with one or a plurality of the individually controllable elements of an array of individually controllable elements. A two-dimensional diffraction grating can, for example, be used to divide the radiation beam into sub-beams. In the present description, the terms "beam of radiation" and "radiation beam" encompass, but are not limited to, the situation in which the beam is comprised of a plurality of such sub-beams of radiation.

The radiation beam B is incident on or emitted from the patterning device (e.g., mask) MA, which is held on the support structure (e.g., mask table) MT, and is modulated by the patterning device MA in accordance with a pattern MP. Having traversed the patterning device MA, the radiation beam B passes through the projection system PS, which focuses the beam B onto a target portion C of the substrate W.

The projection system has a pupil PPU conjugate to the illuminator pupil IPU. Portions of radiation emanate from the intensity distribution at the illuminator pupil IPU and traverse a patterning device pattern without being affected by diffraction at a patterning device pattern create an image of the intensity distribution at the illuminator pupil IPU.

With the aid of the second positioner PW and position sensor IF (e.g., an interferometric device, linear encoder, or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g., after mechanical retrieval from a mask library, or during a scan.

In an example, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. It will be appreciated that the beam B can alternatively/additionally be moveable, while the object table and/or the patterning device can have a fixed position to provide the required relative movement. Such an arrangement can assist in limiting the size of the apparatus. As a further alternative, which can, e.g., be applicable in the manufacture of flat panel displays, the position of the substrate table WT and the projection system PS can be fixed and the substrate W can be arranged to be moved relative to the substrate table WT. For example, the substrate table WT can be provided with a system to scan the substrate W across it at a substantially constant velocity.

Patterning device MA and substrate W may be aligned using patterning device alignment marks M1, M2 and substrate alignment marks P1, P2. Although the substrate alignment marks P1, P2 as illustrated occupy dedicated target portions, they may be located in spaces between target portions (these are known as scribe-lane alignment marks). Similarly, in situations in which more than one die is provided on the patterning device MA, the patterning device alignment marks M1 and M2 may be located between the dies.

The lithographic apparatus can be of a type having two (dual stage) or more substrate and/or patterning devices tables. In such "multiple stage" machines, the additional tables can be used in parallel, or preparatory steps can be carried out on one or more tables while one or more other tables are being used for exposure.

The lithographic apparatus can also be of a type wherein at least a portion of the substrate can be covered by an "immersion liquid" having a relatively high refractive index, e.g., water, so as to fill a space between the projection system and the substrate. An immersion liquid can also be applied to other spaces in the lithographic apparatus, for example, between the patterning device and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

In one example, such as the embodiment depicted in FIG. 1, the substrate W has a substantially circular shape, optionally with a notch and/or a flattened edge along part of its perimeter. In another example, the substrate has a polygonal shape, e.g., a rectangular shape.

Examples where the substrate has a substantially circular shape include examples where the substrate has a diameter of at least 25 mm, at least 50 mm, at least 75 mm, at least 100 mm, at least 125 mm, at least 150 mm, at least 175 mm, at least 200 mm, at least 250 mm, or at least 300 mm. Alternatively, the substrate has a diameter of at most 500 mm, at most 400 mm, at most 350 mm, at most 300 mm, at most 250 mm, at most 200 mm, at most 150 mm, at most 100 mm, or at most 75 mm, Examples where the substrate is polygonal, e.g., rectangular, include examples where at least one side, at least 2 sides or at least 3 sides, of the substrate has a length of at least 5 cm, at least 25 cm, at least 50 cm, at least 100 cm, at least 150 cm, at least 200 cm, or at least 250 cm.

At least one side of the substrate has a length of at most 1000 cm, at most 750 cm, at most 500 cm, at most 350 cm, at most 250 cm, at most 150 cm, or at most 75 cm.

In one example, the substrate W is a wafer, for instance a semiconductor wafer. The wafer material can be selected from the group consisting of Si, SiGe, SiGeC, SiC, Ge, GaAs, InP, and InAs. The substrate can be: a III/V compound semiconductor wafer, a silicon wafer, a ceramic substrate, a glass substrate, or a plastic substrate. The substrate can be transparent (for the naked human eye), colored, or absent a color.

The thickness of the substrate can vary and, to an extent, can depend on the substrate material and/or the substrate dimensions. The thickness can be at least 50 µm, at least 100 µm, at least 200 µm, at least 300 µm, at least 400 µm, at least 500 µm, or at least 600 µm. Alternatively, the thickness of the substrate can be at most 5000 µm, at most 3500 µm, at most 2500 µm, at most 1750 µm, at most 1250 µm, at most 1000 µm, at most 800 µm, at most 600 µm, at most 500 µm, at most 400 µm, or at most 300 µm.

The substrate referred to herein can be processed, before or after exposure, in for example a track (a tool that typically applies a layer of resist to a substrate and develops the exposed resist), a metrology tool, and/or an inspection tool. In one example, a resist layer is provided on the substrate.

It is to be appreciated that, although the description is directed to lithography, the patterned device MA can be formed in a display system (e.g., in a LCD television or projector), without departing from the scope of the present invention. Thus, the projected patterned beam can be projected onto many different types of objects, substrates, display devices, etc.

The depicted apparatus of FIG. 1 could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In a pulse mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

4. Continuous scan mode is essentially the same as pulse mode except that the substrate W is scanned relative to the modulated beam of radiation B at a substantially constant speed and the pattern on the array of individually controllable elements is updated as the beam B scans across the substrate W and exposes it. A substantially constant radiation source or a pulsed radiation source, synchronized to the updating of the pattern on the array of individually controllable elements, can be used.

5. In pixel grid imaging mode, which can be performed using the lithographic apparatus of FIG. 1, the pattern formed on substrate W is realized by subsequent exposure of spots formed by a spot generator that are directed onto patterning device MA. The exposed spots have substantially the same shape. On substrate W the spots are printed in substantially a grid. In one example, the spot size is larger than a pitch of a printed pixel grid, but much smaller than the exposure spot grid. By varying intensity of the spots printed, a pattern is realized. In between the exposure flashes the intensity distribution over the spots is varied.

Combinations and/or variations on the above described modes of use or entirely different modes of use may also be employed.

Example Scatterometry Apparatus

Figure 2A:
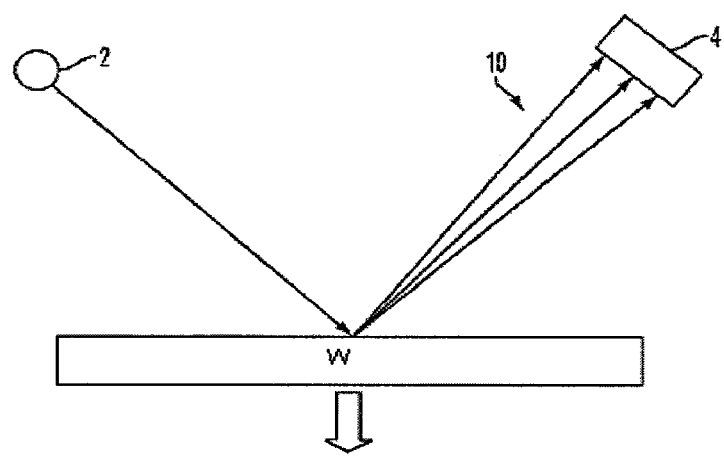
FIGS. 2A to 2C schematically depict the principles of angle-resolved and spectroscopic scatterometry.
Figure 2B:
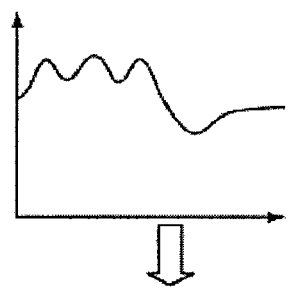
Figure 2C:
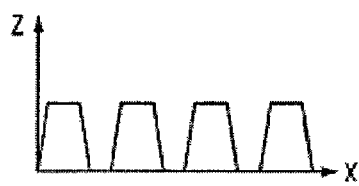

FIGS. 2A-2C schematically depict principles of angle-resolved and spectroscopic scatterometry according to an embodiment of the invention by which one or more properties of the surface of a substrate W may be determined. In an embodiment, referring to FIG. 2A, the scatterometer comprises a radiation source 2 (e.g., a broadband (white light) radiation source), which directs radiation onto a substrate W. The reflected radiation is passed to a sensor 4 (e.g., a spectrometer detector) which measures a spectrum 10 (intensity as a function of wavelength) of the specular reflected radiation. From this data, the structure or profile giving rise to the detected spectrum may be reconstructed, e.g., by Rigorous Coupled Wave Analysis and non-linear regression or by comparison with a library of simulated spectra, as shown in FIGS. 2B and 2C. In general, for the reconstruction, the general form of the structure is known and some parameters are assumed from knowledge of the process by which the structure was made, leaving only a few parameters of the structure to be determined from the scatterometry data.

The scatterometer may be a normal-incidence scatterometer or an oblique-incidence scatterometer. Variants of scatterometry may also be used in which the reflection is measured at a range of angles of a single wavelength, rather than the reflection at a single angle of a range of wavelengths.

Figure 3:
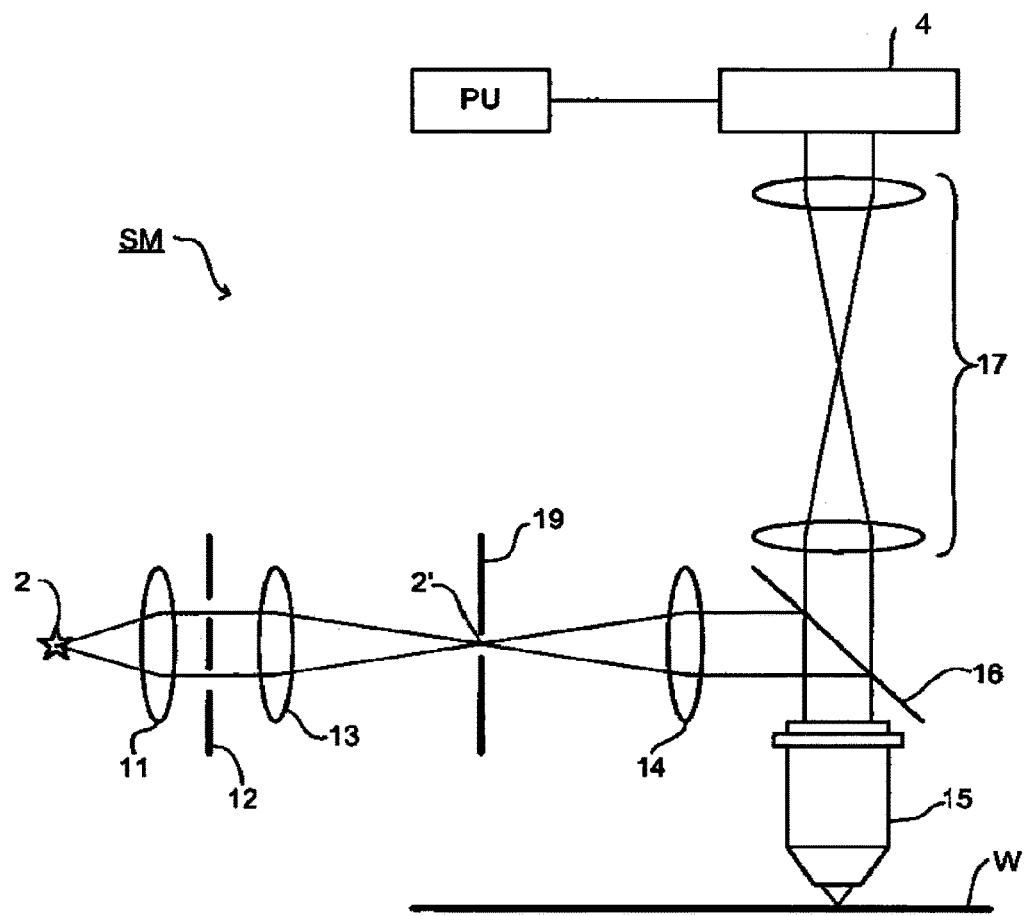
FIG. 3 schematically depicts another example scatterometer.

FIG. 3 schematically depicts a scatterometer according to an embodiment of the present invention. Radiation emitted by a radiation source 2 is collected by illumination system 11-14 and focused onto a spot covering a target on substrate W via an objective 15 and partially reflective mirror 16. The objective 15 has a high numerical aperture (NA), in an embodiment at least 0.9 or at least 0.95. An immersion scatterometer may even have a lens with a numerical aperture over 1. Radiation reflected by the substrate then transmits through partially reflective surface 16 into a detector 4 in order to have the scatter spectrum detected. The detector 4 is located in the back-projected pupil plane of the lens 15 or the pupil plane may instead be re-imaged with auxiliary optics 17 onto the detector 4. The pupil plane is the plane in which the radial position of radiation defines the angle of incidence and the angular position defines the azimuth angle of the radiation. The radiation source 2 may be part of the scatterometer or may simply be conduit of radiation from an outside radiation generator.

In an embodiment, the detector is a two-dimensional detector so that a two-dimensional angular scatter spectrum of the substrate target can be measured. The detector 4 may be, for example, an array of CCD or CMOS sensors, and may have an integration time of, for example, 40 milliseconds per frame.

The detector 4 may measure the intensity of scattered radiation at a single wavelength (or narrow wavelength range), the intensity separately at multiple wavelengths or the intensity integrated over a wavelength range. Furthermore, the detector may separately measure the intensity of transverse magnetic- and transverse electric-polarized radiation and/or the phase difference between the transverse magnetic- and transverse electric-polarized radiation.

Using a broadband radiation source (i.e. one with a wide range of radiation frequencies or wavelengths—and therefore of colors) is possible, which gives a large etendue, allowing the mixing of multiple wavelengths. Several "sources" of radiation may be different portions of an extended radiation source which has been split using fiber bundles. In this way, angle resolved scatter spectra may be measured at multiple wavelengths in parallel. A 3-D spectrum (wavelength and two different angles) may be measured, which contains more information than a 2-D spectrum. This allows more information to be measured which increases metrology process robustness.

The target on substrate W is selected so that it is sensitive to a parameter of the lithographic process to be investigated, for example, focus, dose or overlay. It may be a grating which is printed such that after development, the bars are formed of solid resist lines. The bars may alternatively be etched into the substrate. The scatterometry data of the printed grating can used by processing unit PU to reconstruct the target to derive from it a value for the parameter under investigation. One or more parameters of the ideal target, such as line widths and shapes, may be input to the reconstruction process from knowledge of the printing step and/or other scatterometry processes. Alternatively or additionally, information indicative of the parameter under investigation my derived directly from the scatterometry data, e.g. by a technique such as Principle Component Analysis.

The illumination system of the scatterometer SM can be regarded as formed of two parts: a first part, represented by lenses 11, 13, forms an intermediate image 2' of the radiation source 2, while a second part, represented by lens 14, working with the high-NA lens 15 images the intermediate image 2' onto the substrate W.

In an embodiment, an illumination aperture blade 12 is provided in the first part of the illumination system and is imaged into the back focal plane of the high-NA lens 15. The illumination aperture blade defines an illumination mode, for example annular illumination, suitable for the intended measurement, e.g. overlay. Because the illumination aperture blade 12 blocks some of the spatial frequencies of the source 2, the image of the source on the substrate is broadened and radiation spills outside of the desired target area. Radiation reflected by structures outside the target area may cause noise in the scatterometry data. Therefore, a field stop 19 is provided at the intermediate image 2' of the radiation source 2. The field stop 19 is desirably only slightly larger than the ideal geometric spot width (e.g., diameter) and therefore blocks radiation that is diffracted outside the geometric spot, ensuring the spot projected onto the substrate is as sharp as possible.

It is noted that the field stop 19 also acts as a low-pass filter for the image of the aperture blade 12 in the back focal plane of the high-NA lens 15, thus blurring the illumination mode. This may reduce the angular resolution of the diffraction orders on the detector 4. However, by using an apodized field stop, i.e. one in which the transition from transparent to opaque is gradual rather than step wise, an optimum balance between stray radiation in the image plane and angular resolution of the diffraction orders can be obtained.

Catadioptric Optical Systems Used For Scatterometry

In an embodiment, the scatterometer includes a catadioptric optical system.

The catadioptric optical system may be used as a special objective in a UV-visible scatterometer for critical dimension (CD) and overlay measurements as, for example, depicted in and described below with respect to FIG. 4.

The catadioptric objective may be used together with the illumination system of the scatterometer as, for example, depicted in and described below with respect to FIG. 11.

In an embodiment, the catadioptric optical system may include (i) a mirror system to provide a high numerical aperture and achromatism, and (ii) a nearly afocal refractive element to correct one or more aberrations (such as coma).

A catadioptric optical system in a scatterometer can have several desirable characteristics. For example, a catadioptric optical system can have a very high numerical aperture (such as, for example, approximately 0.95) and operate in a wide spectral range (such as, for example, approximately 193 nanometers to 1050 nanometers). In addition, a catadioptric optical system can produce low obscuration in the sensing branch (approximately 15%). Moreover, a catadioptric optical system can include fewer optical surfaces in the sensing branch compared to a conventional scatterometer, thereby reducing or minimizing scattering and ghost images produced in the sensing branch. Furthermore, a catadioptric optical system has smaller dimensions and weight compared to conventional scatterometers.

An achromatic, high numerical aperture catadioptric optical system in accordance with an embodiment of the present invention includes a convex spherical surface and a concave aspherical surface positioned to receive electromagnetic radiation from the convex spherical surface.

Figure 4:
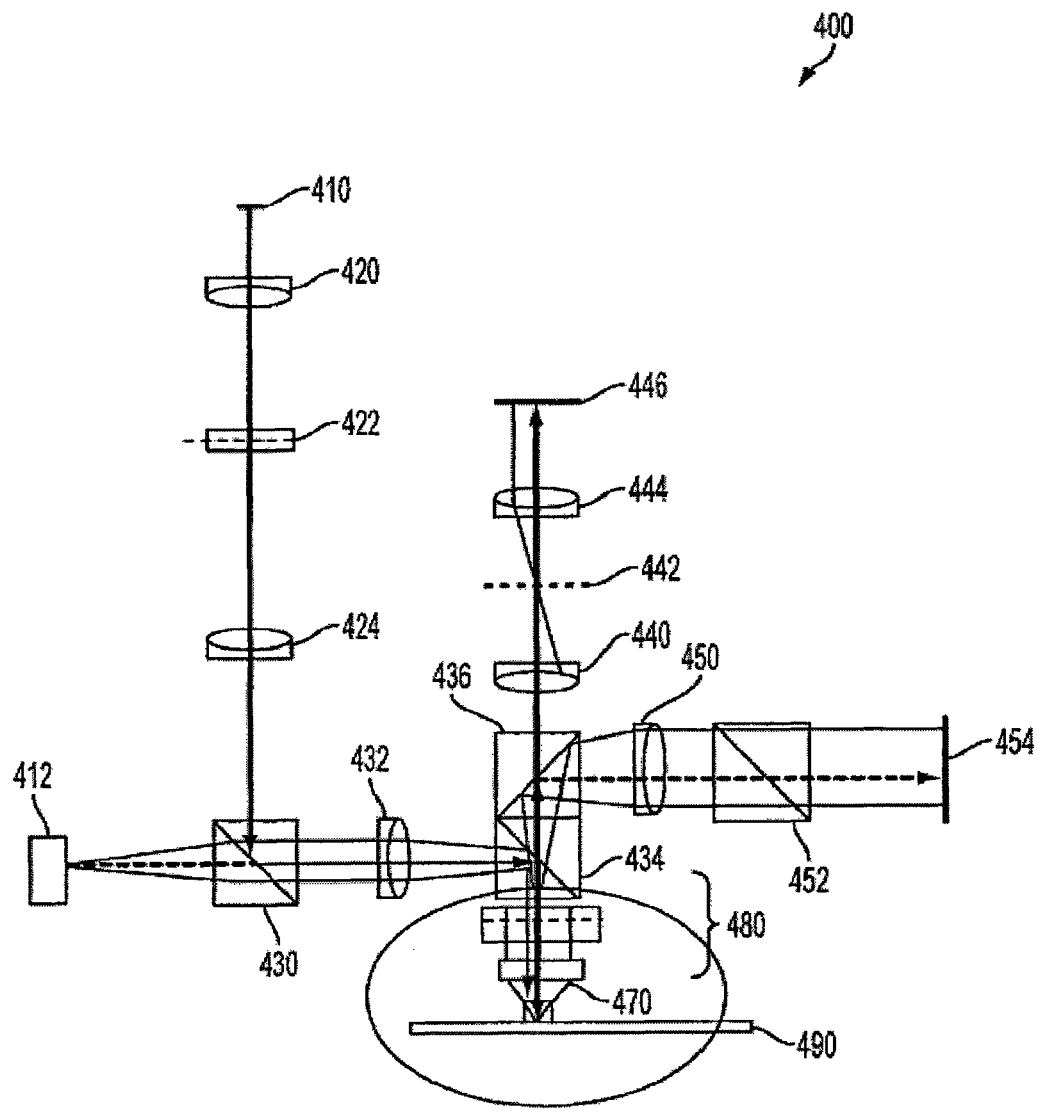
FIG. 4 schematically depicts a sensing and alignment system including a catadioptric optical objective in accordance with an embodiment of the present invention.

FIG. 4 depicts a scatterometry system 400 that can sense one or more properties of the surface of substrate 490. Scatterometry system 400 is comparable to the one shown in FIG. 3. For example, elements 11, 13 and 14 of FIG. 3 are comparable to elements 420, 422, 424, 432 of FIG. 4. Similarly, objective 15 of FIG. 3 may be or include catadioptric optical system 480 of FIG. 4.

System 400 has an alignment branch and a sensing branch and includes a catadioptric optical system 480. In the embodiment depicted in FIG. 4, catadioptric optical system 480 includes a optical element 434 (e.g., a beam splitter) and an objective system 470. The alignment branch, sensing branch, and catadioptric optical system 480 are described in more detail below.

The alignment branch is used to align system 400 with features on a substrate 490. The alignment branch includes an illumination source 412 (such as a wide band light emitting diode (LED)) that provides a first beam of radiation. In an example, the first beam has a spectral range between 450 nanometers and 600 nanometers. The first beam passes through optical elements 430 and 432 and then impinges on an optical element 434. The first beam is then directed through or adjacent objective 470 and focused on a portion of substrate 490. The first beam is then redirected (e.g., reflected and/or refracted) back through optical element 434 (e.g., via objective 470 if the first beam is directed to the substrate via objective 470). A beam splitter 436 directs the first beam through a focusing lens 450 and beam splitter 452, and then onto a first sensor 454 (e.g., a charge coupled device (CCD)). The image of substrate 490, provided by sensor 454, is used to align system 400 with specific portions of substrate 490.

The sensing branch is used to sense or detect the features on the aligned portions of substrate 490 according to known scatterometry techniques, such as the scatterometry techniques described above. The sensing branch includes an illumination source 410 (such as a tungsten illumination source having an interference filter) that provides a second beam of radiation. In an example, the second beam has a bandwidth of approximately 10 nanometers and falls within the spectral range of approximately 300 nanometers to 800 nanometers. The second beam passes through optical elements 420, 422, 424, 430 and lens 432. Optical element 434 then directs the second beam through objective system 470 and onto an aligned portion of substrate 490. The second beam is redirected by the aligned portion of substrate 490 and directed back through objective system 470 and optical element 434. The second beam passes through beam splitter 436, lens 440, aperture 442, and lens 444, and then impinges on a second detector 446 (e.g., second CCD). Second detector 446 provides an image of the aligned portion of substrate 490 that is used to detect features on the surface of substrate 490.

As mentioned above, catadioptric optical system 480 includes optical element 434 and objective system 470. Catadioptric optical system 480 is achromatic in a wide spectral range (such as about 193 nanometers to 1050 nanometers). When used in system 400, catadioptric optical system 480 has low obscuration in the sensing branch (such as approximately 15% by radius). It has smaller dimensions and weight, and only a few surfaces thereby reducing scatter and eliminating ghost images. When used for sensing, objective system 470 can have a high numerical aperture (such as, for example, approximately 0.90 or 0.95) and does not use refractive elements. As a result, objective system 470 operates properly over a wide spectral range (such as about 193 nanometers to 1050 nanometers).

In an embodiment, the alignment branch and the sensing branch may both share catadioptric optical system 480. In an embodiment, catadioptric optical system 480 functions properly within the optical specifications of both the alignment branch and the sensing branch. In such an embodiment, the refractive elements of the alignment branch are situated in a volume that is obscured by a small spherical mirror of the catadioptric optical system 480. A first surface (or group of surfaces) in the alignment branch has a common surface (or surfaces) with a convex reflective surface in the sensing branch. The convex reflective surface can be partly reflective (such as, for example, 80% reflection) or have a spectral-dependent reflection that provides radiation distribution between the sensing and alignment branches. For example, the convex reflective surface can be conditioned (e.g., coated) to cause it to have (i) refractive properties for the electromagnetic radiation from the alignment branch and (ii) reflective properties for the electromagnetic radiation from the sensing branch. Where used in the alignment branch in system 400, catadioptric optical system 480 has substantially no obscuration in the alignment branch. Alternatively, the catadioptric optical system 480 can be used in a system that only includes a sensing branch.

Additional catadioptric optical systems in accordance with embodiments of the present invention are described and illustrated below, for example, in FIGS. 5-9. In each of the embodiments depicted in FIGS. 5-9, collimated electromagnetic radiation from an illumination system is focused onto a small spot (such as approximately 10 microns) on a substrate (e.g., a wafer). Each embodiment can be used for scatterometry, and each embodiment has an extremely wide numerical aperture (such as a numerical aperture of approximately 0.95) and operates in a wide spectral range (such as about 193 nanometers to 1050 nanometers).

Figure 5:
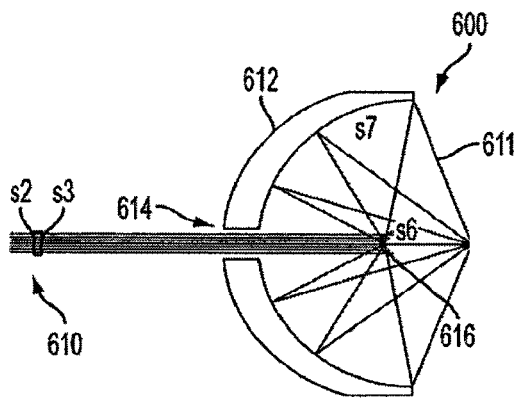
FIGS. 5-8 schematically depict various catadioptric optical systems in accordance with embodiments of the present invention.

FIG. 5 depicts an example catadioptric optical system 600 in accordance with an embodiment. As shown in FIG. 5, catadioptric optical system 600 includes a correcting plate 610, a spherical convex mirror 616, and an aspherical concave mirror 612.

Correcting plate 610 conditions a beam of radiation to correct one or more optical aberrations (such as coma). As shown in FIG. 5, correcting plate 610 includes an aspherical surface s2 and a spherical surface s3. Radiation conditioned by correcting plate 610 passes through a hole 614 in aspherical concave mirror 612 and impinges on spherical convex mirror 616. Spherical convex mirror 616 comprises a spherical reflective surface s6 that is positioned to reflect the radiation conditioned by correcting plate 610. Aspherical concave mirror 612 receives the radiation reflected by spherical reflective surface s6. Aspherical concave mirror 612 comprises an aspherical reflective surface s7 that focuses this radiation on a target portion of the substrate. For example, an example ray 611 reflected by aspherical reflective surface s7 is depicted in FIG. 5.

Figure 6:
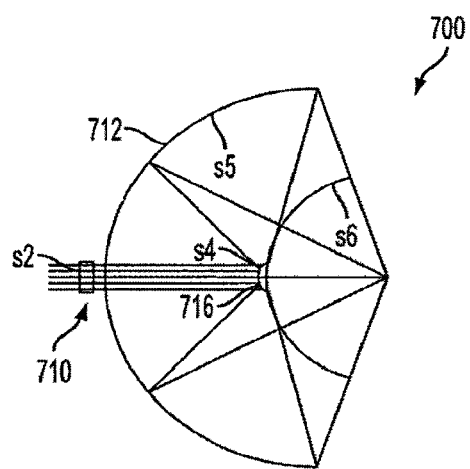

FIG. 6 depicts an example catadioptric optical system 700 in accordance with a further embodiment. As shown in FIG. 6, catadioptric optical system 700 includes a correcting plate 710, a spherical convex mirror 716, and a monolithic glass element 712.

Correcting plate 710 conditions a beam of electromagnetic radiation to correct one or more optical aberrations (such as coma). Correcting plate 710 includes an aspherical surface s2.

Spherical convex mirror 716 comprises a spherical reflective surface s4 that is positioned to reflect the electromagnetic radiation conditioned by correcting plate 710. In the embodiment depicted in FIG. 6, spherical convex mirror 716 is positioned on a surface s6 of monolithic glass element 712. Aspheric surface s5 of monolithic glass element 712 has a reflective portion and a transparent portion. Transparent portion is centered around the optical axis and has a size based on the cross-sectional size of the input beam. As a result, surface s5 passes a beam coming from correcting plate 710, but reflects rays coming from spherical mirror 716. That is, electromagnetic radiation conditioned by correcting plate 710 passes through the transparent portion of surface s5 in monolithic glass element 712 and impinges on spherical convex mirror 716.

Monolithic glass element 712 includes surfaces s4, s5 and s6. Surface s5 of monolithic glass element 712 receives the radiation reflected by spherical convex mirror 716 (surface s4) and reflects this radiation toward a target portion of the substrate. Before impinging on the target portion of the substrate, the radiation traverses surface s6 of monolithic glass element. Rays reflecting off of aspheric reflective surface s5 exit monolithic glass element 712 substantially perpendicularly to surface s6, and are therefore substantially not refracted by surface s6. As a result, catadioptric optical system 700 is achromatic.

Figure 7:
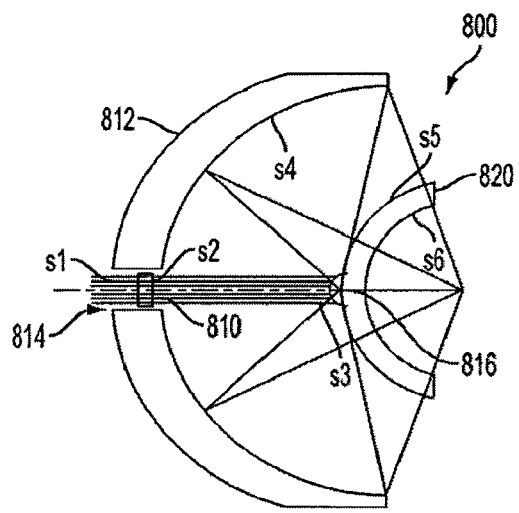

FIG. 7 depicts an example catadioptric optical system 800 in accordance with a further embodiment. As shown in FIG. 7, catadioptric optical system 800 includes a correcting plate 810, a spherical convex mirror 816, an aspherical concave mirror 812, and a element 820.

Correcting plate 810 conditions a beam of radiation to correct one or more optical aberrations (such as coma). Correcting plate 810 includes an aspherical surface s1 and a surface s2. As illustrated in FIG. 7, correcting plate 810 is positioned in a hole 814 of aspherical concave mirror 812.

Spherical convex mirror 816 comprises a spherical reflective surface s3 that is positioned to reflect the radiation conditioned by correcting plate 810. In the embodiment depicted in FIG. 7, spherical convex mirror 816 is positioned on a surface s5 of element 820. Radiation conditioned by correcting plate 810 impinges on spherical convex mirror 816.

Aspherical concave mirror 812 includes aspheric reflective surface s4. Aspherical reflective surface s4 of aspherical concave mirror 812 receives the radiation reflected by spherical convex mirror 816 and reflects this radiation toward element 820 (e.g., a meniscus).

Element 820 includes a first surface s5 and a second surface s6. The radiation reflected by aspherical concave mirror 812 passes through element 820 substantially perpendicularly to both first surface s5 and second surface s6, and is therefore substantially not refracted at either surface of element 820. As a result, catadioptric optical system 800 is achromatic.

Figure 8:
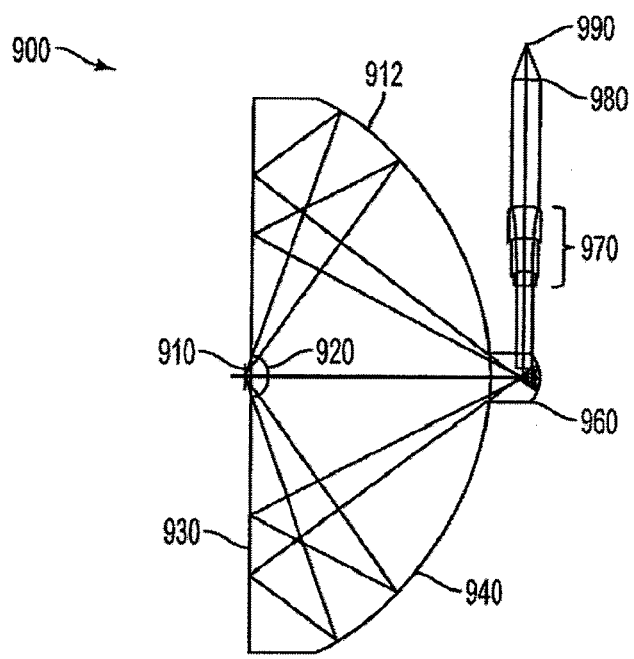

FIG. 8 depicts an illumination system and catadioptric optical system 900 in accordance with a further embodiment. Catadioptric optical system 900 has an illumination numerical aperture of approximately 0.95 and works in a wide spectral range from approximately 300 nanometers to 800 nanometers. Catadioptric optical system 900 creates a small spot (such as, for example, about a 10 micron spot) on a substrate 910.

Catadioptric optical system 900 includes a spherical refractive surface 920, a plane reflective surface 930, an aspherical reflective surface 940, an optical element 960, a group of lenses 970, a subsidiary lens 980, and an illumination source 990 conjugate to the spot on substrate 910. Illumination source 990 provides radiation that propagates through subsidiary lens 980 and lenses 970. Lenses 970 have at least one aspheric surface. Lenses 970 function to correct aberrations (such as coma) of catadioptric optical system 900. Lenses 970 may form an afocal lens group 970. Optical element 960 directs the radiation from lenses 970 to reflect off of plane reflective surface 930. The electromagnetic radiation then reflects off of aspherical reflective surface 940, passes through spherical refractive surface 920, and is focused on substrate 910. The radiation traverses spherical refractive surface 920 in a direction that is substantially perpendicular to surface 920. As a result, catadioptric optical system 900 is achromatic.

Catadioptric optical system 900 can be used to test or sense features of substrate 910. In the sensing mode, catadioptric optical system 900 works as a high numerical aperture Fourier objective, wherein radiation propagates in the opposite direction of that shown in FIG. 8. Specifically, radiation will be redirected by the surface of substrate 910, traverse through catadioptric optical system 900, and impinge upon a CCD located in a plane conjugate with the back focal plane of catadioptric optical system (i.e., the pupil plane). Radiation spots located at different points on the CCD correspond to beams of radiation redirected at different angles from the surface of substrate 910. Using known scatterometry techniques, these spots can be used to analyze features of substrate 910 (such as CD and overlay).

Figure 9:
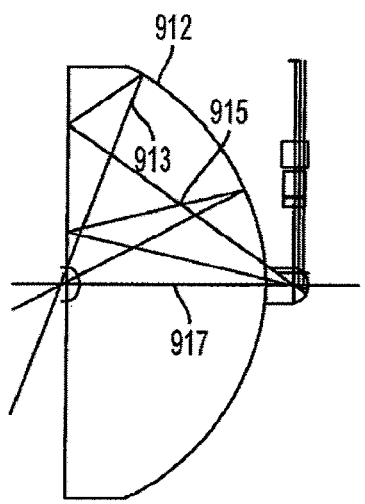
FIG. 9 schematically depicts rays traversing the catadioptric optical system of FIG. 8.

For example, FIG. 9 depicts three redirected beams 913, 915, and 917 (corresponding to redirected rays at about 0, 30, and 72 degrees from the surface of substrate 910) propagating through catadioptric optical system 900 in the sensing mode. The redirected beams create a Fourier pattern in the pupil plane of catadioptric optical system 900.

Aspherical mirror 940, plane mirror 930, and refractive spherical surface 920 can be made from a monolithic glass optical element 912. Monolithic glass optical element 912 can be fabricated from a glass (for example, $SiO_2$) that transmits in a spectral range from approximately 193 nanometers to 1050 nanometers. In this example, plane mirror 930 comprises an annulus with refractive spherical surface 920 positioned in the center of the annulus. Monolithic glass optical element 912 is oriented to cause an illumination spot on substrate 910 to be concentric with plane mirror 930 and refractive spherical surface 920. Optical element 960 can be fabricated from the same material as monolithic glass element 912 and assembled by optically contacting it with monolithic glass element 912.

Figure 10:
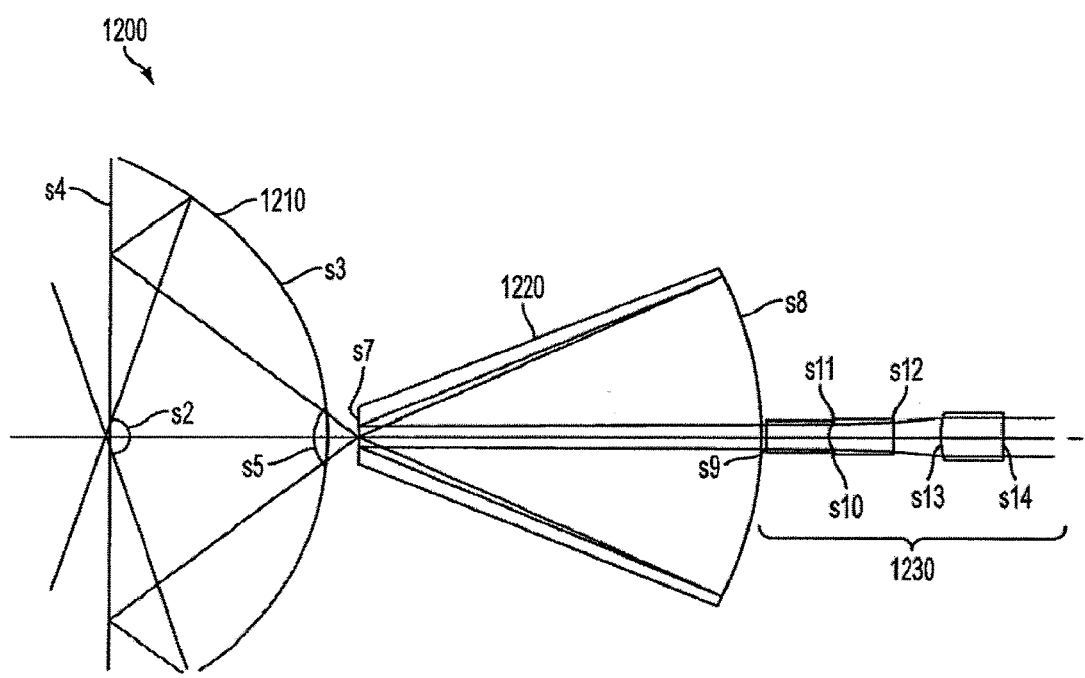
FIG. 10 schematically depicts a catadioptric optical system that transforms from a very high numerical aperture to a low numerical aperture.

FIG. 10 depicts an example catadioptric optical system 1200 in accordance with a further embodiment. Catadioptric optical system 1200 includes a first monolithic glass element 1210, a second monolithic glass element 1220, and a refractive lens group 1230 cascaded together. Monolithic glass element 1210 transitions from a numerical aperture of approximately 0.95 to numerical aperture of approximately 0.4 (and back). Cascading monolithic glass elements 1210 and 1220 transitions from a numerical aperture of approximately 0.95 to a numerical aperture of approximately 0.02.

First monolithic glass element 1210 includes a refractive surface s2, an aspherical reflective surface s3, a plane reflective surface s4, and a refractive surface s5. As illustrated in FIG. 10, refractive surface s2 is positioned in the center of plane reflective surface s4, and refractive surface s5 is positioned in the center of aspherical reflective surface s3.

Second monolithic glass element 1220 includes a reflective surface s7 and a reflective surface s8 surfaces s7 and s8 each include a central, transparent portion.

Refractive lens group 1230 includes optical surfaces s9, s10, s11, s12, s13, and s14, which are positioned and shaped to correct one or more aberrations (such as coma).

This optical design functions similar to the designs depicted in FIGS. 8 and 9, but has just one aspheric surface (aspherical reflective surface s3 of first monolithic glass element 1210) and a wider spectral range (about 193 to 1050 nanometers).

For example, radiation enters catadioptric optical system 1200 through refractive lens group 1230. The radiation passes through refractive lens group 1230, and then through the central, transparent portion of reflective surface s8.

The radiation passing through the central, transparent portion of reflective surface s8 is reflected by reflective surface s7 and then received by reflective surface s8. Reflective surface s8 focuses the radiation into a focused spot of radiation that passes through the central, transparent portion of reflective surface s7. That is, second monolithic glass element 1220 is configured to provide a focused spot of radiation.

Refractive surface s5 of first monolithic glass element 1210 is positioned to be concentric with the focused spot of radiation from second monolithic glass element 1220. Consequently, radiation from second monolithic glass element 1220 enters first monolithic glass element 1210 substantially perpendicularly to refractive surface s5. Reflective surface s4 receives this radiation and reflects it toward aspherical reflective surface s3. Aspherical reflective surface s3 focuses the radiation onto a focused spot on a substrate (not specifically shown in FIG. 10). Refractive surface s2 is positioned to be concentric to the focused spot on the substrate, thereby causing the radiation to exit first monolithic glass element 1210 substantially perpendicular to refractive surface s2.

Because radiation enters and exits first monolithic glass element 1210 substantially perpendicularly to refractive surfaces s5 and s2, catadioptric optical system is substantially achromatic, i.e., having a spectral range of approximately 193 to 1050 nanometers.

A metrology tool, such as a scatterometer as discussed above, may operate in wide spectral range (e.g., approximately 193 to 1050 nanometers) with a high numerical aperture. However, such a metrology tool may have effectively a shorter spectral band (e.g., 300-800 nm) because the illumination system for the metrology tool is unable to provide the wide spectral range. This is due to the chromatic limitation of refractive elements in the illumination system.

Figure 11:
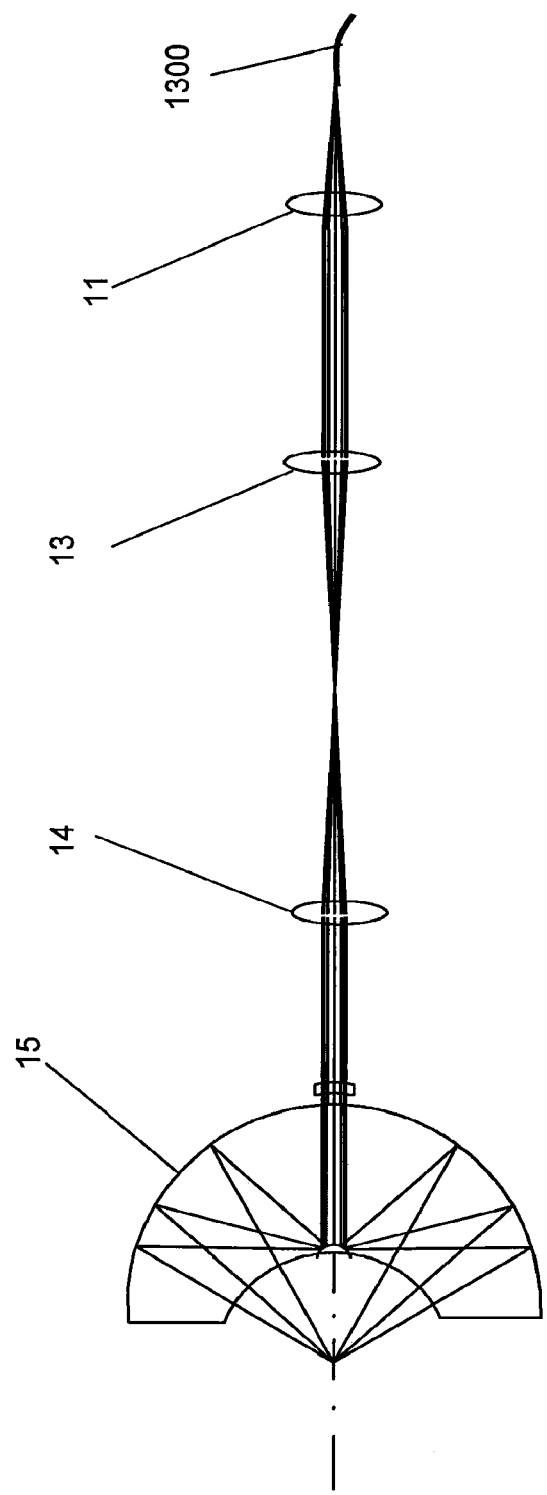
FIG. 11 schematically depicts an illumination branch of a scatterometer according to an embodiment of the invention.

FIG. 11 shows a schematic view of a scatterometer according to an embodiment of the invention. FIG. 11 essentially shows the illumination system of the scatterometer which supplies radiation to the objective 15 (which as discussed above may be, or include, a catadiopric optical system). Referring to FIG. 11, the illumination system includes an illumination fiber 1300 to bring radiation from an optical source 2 (not shown) to the illumination system. The illumination system further includes a condenser lens 11 and relay lenses 13 and 14.

To enable the illumination system to provide a wide spectral range, an achromatic condenser lens 11 with input NA>0.05 that can effectively collect light from high NA illumination fiber 1300 should be provided.

According to an embodiment of the invention, a catadioptric optical system is provided as condenser lens 11, hereinafter the catadioptric condenser lens. It performs the function of a condenser lens but is achromatic and operates in wide spectral range from about 193 to 1050 nm, Design parameters of the catadioptric condenser lens can be selected in order to have minimal central obscuration. In an embodiment, the obscuration of the catadioptric condenser lens may match that of the objective 15. For example, the obscuration may be less than or equal to that in the objective 15. In that case the catadioptric condenser lens would not introduce additional losses of radiation in the system than that would be provided by the objective 15. In an embodiment, the obscuration may be up to 20% more than that of the objective. In an embodiment, the obscuration is approximately 15% or less by pupil radius. Relay lenses 13 and 14 may be fabricated as doublets from $CaF_2$ and/or $SiO_2$ and provide matching of illumination field size downstream of the catadioptric condenser lens and the size of the pupil of the objective.

Figure 12:
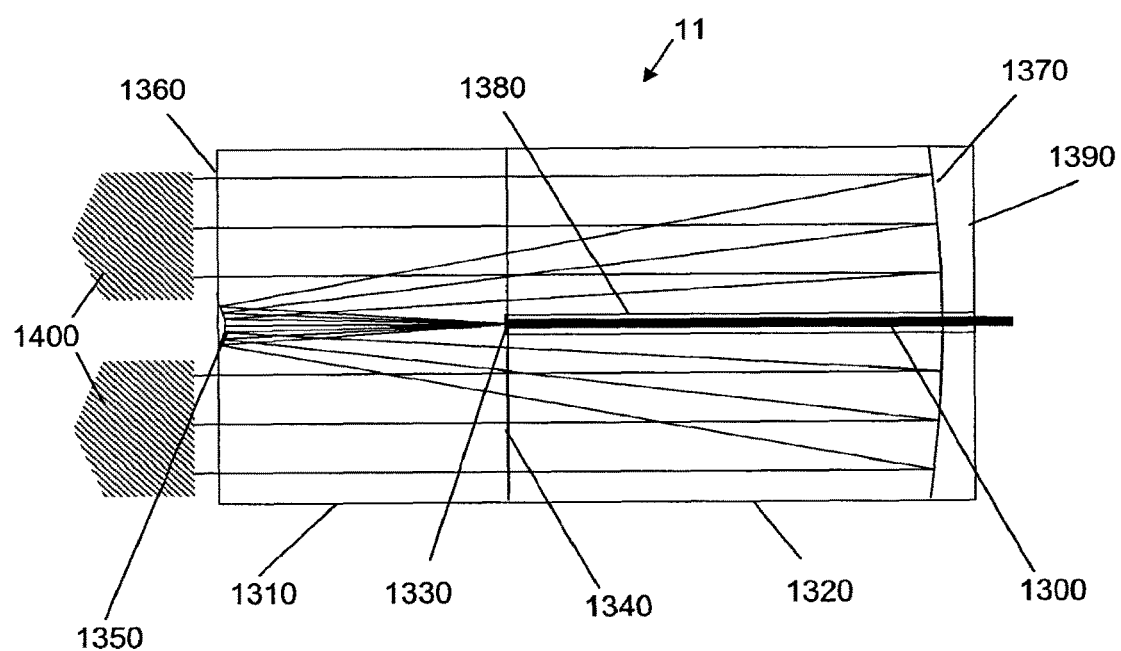
FIG. 12 schematically depicts a catadioptric condenser lens according to an embodiment of the invention.

FIG. 12 schematically depicts a catadioptric condenser lens 11 according to an embodiment of the invention. The catadioptric condenser lens 11 includes a first transparent material block 1310 and a second transparent material block 1320. The first block 1310 and the second block 1320 may be separate optical parts fabricated into a single piece at an interface 1340 or may be a monolithic element of transparent material. The material of the first block 1310 and/or the second block 1320 may be fused silica ($SiO_2$), calcium fluoride ($CaF_2$) or glass.

The first block 1310 comprises a spherical mirror 1350. In an embodiment, the first block 1310 has an output surface 1360 (e.g., a flat surface) in which there is a cavity that forms the spherical mirror 1350. The cavity may be, e.g., silvered. In an embodiment, the cavity may be filled with a material. The material in the cavity may be different than that of the first block 1310, in which case silvering may not be necessary.

The second block 1320 comprises a reflective surface 1370. In an embodiment, the reflective surface 1370 is aspherical. In an embodiment, the reflective surface 1370 may be embedded in the second block 1320 as shown. This may be produced, for example, by contacting a silvered first part of second block 1320 with a conforming second part of second block 1320 having surface 1390. The second part of second block 1320 may be of a different material than that of the first part of second block 1320, in which case silvering may not be necessary. In an embodiment, the surface 1390 may be the reflective surface 1370.

The second block 1320 further comprises a hole 1380 extending into the second block 1320 from the surface 1390 of the second block 1320. In an embodiment, the hole is cylindrical.

Optical fiber 1300 extends into the hole 1380 of the second block 1320 and terminates at outlet 1330 of the optical fiber 1300. In an embodiment, the outlet 1330 ends at the interface 1340 between the first block 1310 and the second block 1320. The outlet 1330 of illumination fiber 1300 acts as an input illumination source. In an embodiment, optical fiber 1300 comprises a cylindrical hollow pipe with a reflective internal surface to deliver illumination radiation. In an embodiment, the outlet 1330 is between the mirror 1350 and the reflective surface 1370 and in an embodiment, about midway or closer to the mirror 1350.

Radiation from the outlet 1330 is reflected from mirror 1350, propagates through all or part of the first block 1310 and the second block 1320, and then reflects from reflective surface 1370 to create a collimated beam of radiation 1400 passing through the output surface 1360. Because the beam is reflected around the mirror 1350, the beam 1400 has a central obscuration. In an embodiment, output surface 1360 is substantially perpendicular to the direction of the beam from the reflective surface 1370. This facilitates an achromatic beam. For example, output surface 1360 is flat.

An example optical prescription of the catadioptric condenser lens is presented in Table 1 below.

TABLE 1

Example optical prescription for a catadioptric condenser lens - reflective surface 1370 is conical with K = −0.8431, the diameter of optical fiber 1300 is assumed to be 200 μm, the material of the catadioptric condenser lens is UV fused silica, and the output beam 1400 diameter is 4.8 mm.

| Surface # | Surface Type | Y Radius | Thickness | Glass | Mode | Y Semi-Aperture |
|---|---|---|---|---|---|---|
| Object | Sphere | Infinity | Infinity | | Refract | |
| Stop | Sphere | Infinity | 10.0311 | Silica | Refract | 2.4000 |
| 2 | Conic | −23.0688 | −10.0311 | Silica | Reflect | 2.4323 |
| 3 | Sphere | −4.8156 | 4.0000 | Silica | Reflect | 0.3497 |
| 4 | Sphere | Infinity | 0.0000 | | Refract | 0.1022 |
| Image | Sphere | Infinity | 0.0000 | | Refract | 0.1022 |

The design shown and described in FIG. 12 and Table 1 has a central obscuration of about ~15% to match the obscuration in the objective 15. Design parameters can be scaled or modified to meet packaging needs of a specific metrology tool (e.g., depending on fiber diameter, objective pupil size, magnification of the relay system, etc.).

In an embodiment, a space between the reflective surface 1350 and the reflective surface 1370 and at least within an outer lateral boundary of reflective surface 1350 or reflective surface 1350 may be filled by gas (e.g., air or nitrogen) or liquid and illumination fiber 1300 is imbedded inside of a hollow mounting pipe surrounded by the gas or liquid. The pipe is connected to the center of reflective surface 1370 and extends at least into the gas or liquid between reflective surface 1350 and reflective surface 1370. In a variant, the mounting pipe may have a reflective internal surface and the illumination fiber 1300 terminates at the entrance of the pipe, as similarly described below with respect to FIG. 13. The radiation would enter the pipe, reflect from the internal surface, and output from outlet 1330.

Figure 13:
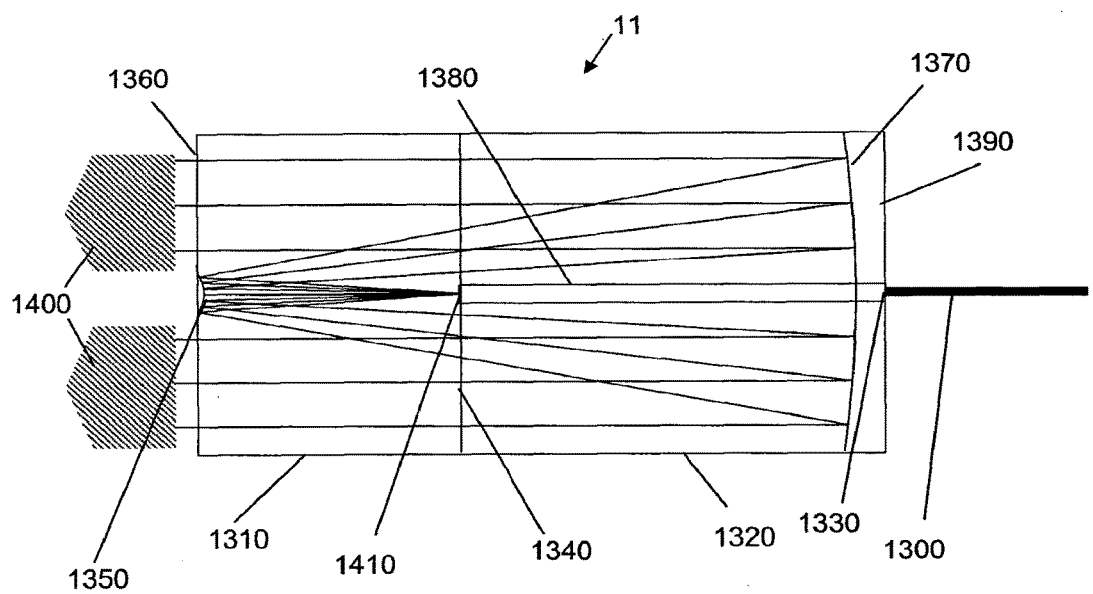
FIG. 13 schematically depicts a catadioptric condenser lens according to an embodiment of the invention.

In an embodiment, referring to FIG. 13 which is similar in many respects to FIG. 12, the optical fiber 1300 is removed from the hole 1380, which is filled with an optical medium (e.g., a transparent material such as glass or a liquid) with a higher refractive index than the material in second block 1320. The outlet 1330 is adjacent to or contacts the radiation exit of the hole 1380. Thus, the hole 1380 acts as a wave guide to deliver illumination radiation to point 1410.

CONCLUSION

Catadioptric optical systems for a metrology tool, such as a scatterometer, have been described. While various embodiments of the present invention have been described above, it should be understood that they have been presented by way of example only, and not limitation. It will be apparent to persons skilled in the relevant art that various changes in form and detail can be made therein without departing from the spirit and scope of the invention. For example, one or more features of an embodiment described herein may combined with or replace one or more features of another embodiment described herein. For example, a catadioptric optical system described above for the objective 15 may be used in the illumination system if suitable modified to output a collimated beam.

A person skilled in the relevant art(s) can modify and re-optimize the above-described embodiments to better comply with a fabrication process of or optics included in the sensing and the alignment branches. For example, convex spherical mirrors 616, 716, 816, and 1350 (of FIGS. 5, 6, 7 and 12, respectively) can be replaced by concave or aspherical mirrors. These, and other modifications, of the above-described embodiments will become apparent to a person skilled in the relevant art(s), and are intended to be within the spirit and scope of the present invention.

In an embodiment, there is provided a metrology tool, comprising: an objective to deliver radiation to a surface and to receive radiation redirected by the surface; a detector to receive the redirected radiation from the objective; and an illumination system to deliver the radiation for redirection to the objective, the illumination system comprising an illumination system catadioptric optical system.

In an embodiment, the objective comprises an objective catadioptric optical system. In an embodiment, the metrology tool is a scatterometer. In an embodiment, the illumination system catadioptric optical system, comprises: a first reflective surface positioned and configured to reflect radiation; a second reflective surface positioned and configured to reflect radiation reflected from the first reflective surface as a collimated beam, the second reflective surface having an aperture to allow transmission of radiation through the second reflective surface; and a channel structure extending from the aperture toward the first reflective surface and having an outlet, between the first reflective surface and the second reflective surface, to supply radiation to the first reflective surface. In an embodiment, the second reflective surface forms or is on a surface of a first solid transmissive element part and the channel structure comprises a channel aperture through the first solid transmissive element part. In an embodiment, the metrology tool is configured to transmit all wavelengths of radiation from the range of approximately 193 to 1050 nanometers. In an embodiment, the metrology tool is configured to obscure approximately 15% or less of the radiation by pupil radius.

In an embodiment, there is provided a catadioptric optical system, comprising: a first reflective surface positioned and configured to reflect radiation; a second reflective surface positioned and configured to reflect radiation reflected from the first reflective surface as a collimated beam, the second reflective surface having an aperture to allow transmission of radiation through the second reflective surface; and a channel structure extending from the aperture toward the first reflective surface and having an outlet, between the first reflective surface and the second reflective surface, to supply radiation to the first reflective surface.

In an embodiment, the second reflective surface forms or is on a surface of a first solid transmissive element part. In an embodiment, the first reflective surface forms or is on a surface of a second solid transmissive element part adjacent the first solid transmissive element part. In an embodiment, the channel structure comprises a channel aperture through the first solid transmissive element part. In an embodiment, the outlet is at an interface between the first solid transmissive element part and the second solid transmissive element part. In an embodiment, the first and second solid transmissive element parts are portions of a monolithic solid transmissive element. In an embodiment, a fluid surrounds the channel structure, extends between the first and second reflective surfaces, and is located at least within an outer lateral boundary of the first reflective surface or the second reflective surface. In an embodiment, the catadioptric optical system further comprises an optical fiber extending in or forming the channel structure. In an embodiment, the first reflective surface comprises a convex reflective surface. In an embodiment, the beam from the second reflective surface passes through a surface substantially perpendicular to the beam direction.

In an embodiment, there is provided a metrology method, comprising: delivering radiation to a surface using an objective; receiving radiation redirected by the surface using the objective; detecting a parameter of the surface using the redirected radiation from the objective; and delivering the radiation for redirection to the objective using a catadioptric optical system.

In an embodiment, the objective comprises a catadioptric optical system. In an embodiment, the objective is part of a scatterometer. In an embodiment, delivering the radiation comprises: reflecting radiation using a first reflective surface of the catadioptic optical system; and reflecting radiation reflected from the first reflective surface using a second reflective surface to form a collimated beam, the second reflective surface having an aperture to allow transmission of radiation through the second reflective surface, wherein a channel structure extends from the aperture toward the first reflective surface and has an outlet, between the first reflective surface and the second reflective surface, to supply radiation to the first reflective surface.

Furthermore, it is to be appreciated that the description may set forth one or more but not all exemplary embodiments of the present invention as contemplated by the inventor(s), and thus, is not intended to limit the present invention and the appended claims in any way. Thus, the breadth and scope of the present invention should not be limited by any of the above-described exemplary embodiments, but should be defined only in accordance with the following claims and their equivalents.

The invention claimed is:

1. A metrology tool, comprising:
a metrology objective configured to deliver metrology radiation to a surface and to receive metrology radiation redirected by the surface;
a detector configured to receive the redirected metrology radiation from the objective to facilitate a metrology measurement; and
an illumination system configured to deliver the metrology radiation for redirection to the metrology objective, the illumination system comprising an illumination system catadioptric optical system that operates through and outside the range of about 300 to 800 nm wavelength metrology radiation.

2. The metrology tool of claim 1, wherein the metrology objective comprises an objective catadioptric optical system.

3. The metrology tool of claim 1, wherein the metrology tool is a scatterometer.

4. The metrology tool of claim 1, wherein the illumination system catadioptric optical system is configured to output a substantially collimated beam of the metrology radiation toward the metrology objective.

5. The metrology tool of claim 1, wherein the illumination system catadioptric optical system, comprises:
a first reflective surface positioned and configured to reflect metrology radiation;
a second reflective surface positioned and configured to reflect metrology radiation reflected from the first reflective surface as a substantially collimated beam, the second reflective surface having an aperture to allow transmission of metrology radiation through the second reflective surface; and
a channel structure extending from the aperture toward the first reflective surface and having an outlet, between the first reflective surface and the second reflective surface, to supply metrology radiation to the first reflective surface.

6. The metrology tool of claim 5, wherein the second reflective surface forms or is on a surface of a first solid transmissive element part.

7. The metrology tool of claim 6, wherein the channel structure comprises a channel aperture through the first solid transmissive element part.

8. The metrology tool of claim 6, wherein the first reflective surface forms or is on a surface of a second solid transmissive element part adjacent the first solid transmissive element part.

9. The metrology tool of claim 8, wherein the outlet is at an interface between the first solid transmissive element part and the second solid transmissive element part.

10. The metrology tool of claim 8, wherein the first and second solid transmissive element parts are portions of a monolithic solid transmissive element.

11. The metrology tool of claim 5, wherein a fluid surrounds the channel structure, extends between the first and second reflective surfaces, and is located at least within an outer lateral boundary of the first reflective surface or the second reflective surface.

12. The metrology tool of claim 5, further comprising an optical fiber extending in or forming the channel structure.

13. The metrology tool of claim 5, wherein the first reflective surface comprises a convex reflective surface.

14. The metrology tool of claim 5, wherein the beam from the second reflective surface passes through a surface substantially perpendicular to the beam direction.

15. The metrology tool of claim 1, wherein the metrology objective and/or the illumination system are configured to transmit all radiation wavelengths from the range of approximately 193 to 1050 nanometers.

16. The metrology tool of claim 1, wherein the illumination system is configured to output metrology radiation that has its cross-section obscured approximately 15% or less.

17. A metrology method, comprising:
delivering metrology radiation to a surface using a metrology tool objective;
receiving metrology radiation redirected by the surface using the metrology tool objective;
detecting a parameter of the surface using the redirected metrology radiation from the metrology tool objective; and
delivering the metrology radiation for redirection to the metrology tool objective using a catadioptric optical system that operates through and outside the range of about 300 to 800 nm wavelength metrology radiation.

18. The metrology method of claim 17, wherein the catadioptric optical system outputs a substantially collimated beam of the metrology radiation towards the metrology objective.

19. The metrology method of claim 17, wherein the metrology tool objective comprises a catadioptric optical system.

20. The metrology method of claim 17, wherein delivering the metrology radiation comprises:
- reflecting metrology radiation using a first reflective surface of the catadioptric optical system; and
- reflecting metrology radiation reflected from the first reflective surface using a second reflective surface to form a substantially collimated beam, the second reflective surface having an aperture to allow transmission of metrology radiation through the second reflective surface,
- wherein a channel structure extends from the aperture toward the first reflective surface and has an outlet, between the first reflective surface and the second reflective surface, to supply metrology radiation to the first reflective surface.

\* \* \* \* \*